United States Patent [19]

Ring

[11] Patent Number: 5,218,965
[45] Date of Patent: Jun. 15, 1993

[54] APPARATUS FOR CARRYING A SENSOR IN A CONNECTOR FOR A CATHETER ADAPTER

[75] Inventor: Wallace H. Ring, Salt Lake City, Utah

[73] Assignee: Becton, Dickinson and Company, Franklin Lakes, N.J.

[21] Appl. No.: 620,994

[22] Filed: Dec. 3, 1990

[51] Int. Cl.⁵ .................................................. A61B 5/02
[52] U.S. Cl. .................................. 128/673; 128/748; 73/866.5
[58] Field of Search ............... 128/637, 748, 672–675; 73/866.5, 756

[56] References Cited

U.S. PATENT DOCUMENTS

| 4,763,648 | 8/1988 | Wyatt | 128/673 |
| 4,920,972 | 5/1990 | Frank et al. | 128/675 |
| 4,936,310 | 6/1990 | Engström et al. | 128/673 |
| 5,086,777 | 2/1992 | Hishii | 128/637 |
| 5,097,841 | 3/1992 | Moriuchi et al. | 128/675 |

FOREIGN PATENT DOCUMENTS

| 0215528 | 3/1987 | European Pat. Off. . |
| 0315526 | 6/1989 | European Pat. Off. . |
| 0330011 | 8/1989 | European Pat. Off. . |
| 0360286 | 9/1989 | European Pat. Off. . |

Primary Examiner—Lee S. Cohen
Assistant Examiner—Robert L. Nasser, Jr.
Attorney, Agent, or Firm—Aaron Passman; Michael G. Schwarz

[57] ABSTRACT

A connector carrying a sensor for placement in a catheter adapter has proximal and distal parts with a passage therebetween. The distal part detachably fits within a catheter adapter. The connector, when attached to the adapter, places the passage in fluid communication with and near a catheter lumen. A sensor on the connector within the distal part is exposed to the passage for fluid communication with the lumen. The sensor mounts on a tube or in an inside wall of the distal part and extends within the passage and partially through the distal part to monitor pressure with a first side of the sensor exposed to the passage and a second side of the sensor covering an exit from the connector near the proximal part. The second side is vented to atmospheric pressure and a sensor signal communication means connects the sensor to pass signals from the sensor through the exit. A sleeve extends distally on the connector for threaded engagement with a male luer on the adapter allowing fluid tight communication between a cavity within the adapter and the passage. The distal part substantially fills the cavity reducing the hydraulic column volume in the lumen and the passage. A method places a catheter into a human or animal to provide access to dynamic pressure, measures atmospheric pressure with a sensor carried on a connector, sets the signal response of the sensor measurement to a datum for atmospheric pressure applied to first and second sides and attaches the connector to the adapter to fit the distal part into the cavity in the adapter so gas within the cavity and the passage escapes to provide a hydraulic column substantially free of gas.

12 Claims, 3 Drawing Sheets

APPARATUS FOR CARRYING A SENSOR IN A CONNECTOR FOR A CATHETER ADAPTER

FIELD OF THE INVENTION.

This invention relates to sensors for use within an adapter of a catheter, and more particularly to a connector for carrying the sensor in fluid communication with a catheter lumen.

BACKGROUND

Catheters have been inserted into humans and animals or monitoring and treatment purposes and such catheters have to be small in size and flexible in structure in order to function without irritating the body part into which they are placed. Typically, catheters are used to infuse medications or remove samples for purposes of analysis. Multilumen catheters are sometimes used to infuse medication and remove samples at the same time.

If a sample is removed for purposes of analysis, it has to be taken to a laboratory, where the analysis is made so results can be transmitted to the doctor. Delay in performing the analysis and transmitting results sometimes can be fatal to the patient. A use for a catheter is for access to the vasculature for a hydraulic column that transmits pressure readings to an external pressure sensor. Hydraulic columns have problems of air bubbles, kinks in the column tubing and blood clots, each of which tend to affect the reliability, waveform fidelity and the accuracy and precision of the readings.

Current technology uses a 20 gauge catheter to introduce therapy or provide diagnosis. This size is easily inserted and used without irritation or injury to the body. Twenty gauge catheters are commonly used on all but pediatric patients in the peripheral vessels without problems of introduction or irritation. A pressure sensor associated with a 20 gauge catheter provides an easy placement but does not eliminate hydraulic column difficulties. Typical of cumbersome external pressure sensors is the unit shown in U.S. Pat. No. 4,825,876 which has a flow through passage to which a sensor is connected in fluid communication. External pressure sensors are typical separated from the patient to prevent damage or dislodgement when the patient moves. The size of such external pressure sensors are typically two or three times a standard female luer.

Catheters having sensors are known and include sensors mounted at the distal tip of the catheter. U.S. Pat. No. 3,710,781 shows a catheter tip pressure sensor wherein a pair of elongate pressure sensor elements are mounted on opposite sides of a support. This is done to permit as large a sensor area as practical for purposes of providing accurate reproductions of blood pressure waveforms. U.S. Pat. No. 3,545,275 shows a device responsive to impedance used for measuring pressure with a miniaturized sensor. The sensor is responsive to diaphragm fluctuations in the distal part of a small diameter tube.

A small probe is disclosed in U.S. Pat. No. 3,811,427 wherein a pair of electrodes are mounted in a liquid filled chamber and are sensitive to fluctuations in a diaphragm mounted at the distal part of a catheter tube. The probe is said to be smaller than one millimeter. Two embodiments are shown. Each has a diaphragm in the distal part of the catheter and a longitudinal separator which carries the pressure responsive means and isolates the liquid from the remainder of the catheter such that fluctuations in the diaphragm are transmitted to the separator which is generally longitudinally disposed.

U.S. Pat. No. 4,722,348 shows a semiconductor mounted within a tubular housing in the part of the catheter tube and having a pressure inlet. Sealant protects the semiconductor which is held to the support by the double face adhesive tape which also carries the electrical conductors. U.S. Pat. No. 4,809,704 discloses catheters with the sensor mounted in the tip of the catheter supported on a base by a potting resin carried within the catheter tube. The resin is a urethane or silicone material about the sensor with appropriate openings for sampling. Assembly of the sensors within the catheters has been slow and labor intensive and the wiring to the sensor is difficult and subject to serious signal and noise.

The offset pressure due to changes in atmospheric pressure has to be accounted for in that the reference side of the sensor is considered a zero pressure. U.S. Pat. No. 4,672,974 has an apparatus with a port for a substitute reference pressure and an external pressure gauge for measuring the mean pressure through an auxiliary lumen of the catheter. Thus, a known pressure can be substituted for atmospheric pressure in the process of rezeroing the offset pressure. U.S. Pat. No. 4,712,566 has a sensor carried on a guide which is moveable in and out of the catheter tube so that the in vivo side of the sensor may be brought into the catheter removed from blood pressure and subjected to a generated pressure during calibration. The guide and catheter cooperate with one another to seal off the sensor during rezeroing.

U.S. Pat. No. 4,854,326 has an impedance variable transducer with a technique for zeroing the in vivo transducer by varying the static pressure in a reservoir connected to the transducer. Thus, changes in the height of the reservoir can be used to adjust the zero point of the transducer. This approach, although feasible, introduces another variable into the system. In addition, a gas retaining flexible membrane has to be located in the liquid filled lumen to the reservoir. The membrane is to separate the liquid from the gas filled lumen. The flexible membrane is said to prevent oscillating movement of the liquid in the lumen as a result of the interchange of energy by the liquid, the displacement of the diaphragm in the transducer and the compliance of the lumen about the liquid. Isolation is not the purpose of the flexible membrane.

U.S. Pat. No. 3,565,056 shows a catheter for placement within a body and an external part on the catheter connected to a domed chamber substantially filled with a strain gauge sensor. A saline solution is supplied to fill the chamber and the catheter during pressure measurement via a conduit passing through parts of the chamber. The conduit passes through of a wall of the chamber to fill the chamber and the catheter at a slow rate with neglible back pressure.

A large part of the problem with pressure transducers is to provide a hydraulic column between the body and the sensor. That is to say that structure should allow prompt and thorough debubbling of the catheter lumen to the body and the associated passage to the sensor. The '056 patent discloses plumbing for a sensor chamber which allows the slowly filled chamber and catheter to block flow of bodily fluid into the catheter. External sampling and means for permitting air within the system to escape are not disclosed. The formation of a solid hydraulic column between the body and the sensor can not be quickly and easily accomplished.

The '056 teaches the profusion of saline solution at a low rate to control filling of the domed chamber. Pressure changes within the domed chamber are claimed to be neglible. An extremely small passage is provided in order to choke the flow entering the dome chamber. It is contemplated that the catheter be flushed prior to insertion into the vein or artery in order to prevent or eliminate air embolism. Consequently, the disclosure of '056 does not suggest or teach the idea of connecting to a standard connector on the proximal part of an inserted over the needle catheter and adapter. The '056 does not teach how a passage extending from the distal part to the proximal part of a connector facilitates forming a hydraulic column. In addition, there is no teaching of the method of removing the connector and sensor from the catheter adapter in order to have atmospheric pressure on both sides of a pressure transducer for purposes of rezeroing.

SUMMARY OF THE INVENTION

A connector carrying a sensor for placement in a catheter adapter may have a proximal part and a distal part with a passage therebetween. The distal part is preferably shaped to detachably connect with and fit within an adapter for a catheter. The connector, when attached to the adapter, places the passage in fluid communication with and near a lumen of the catheter. A sensor can be mounted on the connector within the distal part thereof and is exposed to the passage for fluid communication with the lumen.

The sensor in a preferred embodiment mounted on a tube extending within the passage and partially through the distal part. The sensor is positioned on the tube to monitor pressure with a first side of the sensor exposed to the passage and a second side of the sensor covering a channel through the tube. The tube may extend through the passage from the sensor to an exit from the connector near the proximal part. The tube is preferably vented to an atmospheric pressure source near the exit and the channel has a sensor signal communication means connected to the sensor and passing through the tube for transmitting signals from the sensor through the exit. The sensor is most preferably a pressure responsive semiconductor sealed across the channel to separate the pressure in the passage from the pressure in the channel. The sensor signal communication means can have a plurality of conductors insulated from one another and arranged to transmit electrical signals from the sensor through the exit.

Alternatively, the sensor mounts to an inside wall of the passage within the distal part thereof, the sensor is located substantially within the inside wall with a first side thereof exposed to the passage and a second side covering an opening through the inside wall and vented at an exit near the proximal part to an atmospheric pressure source. The opening extends within the inside wall from the sensor to the proximal part and may preferably be a groove having a sensor signal communication means and passing therewithin for transmitting signals from the sensor through the exit. The sensor signal communication means may seal the groove separating the pressure in the passage and the pressure in the groove. The connector may have a sleeve with a female luer thread rotatably carried about the proximal part. The sleeve extends distally for threaded engagement with a male luer thread of the adapter allowing fluid tight communication between the distal part and the passage.

The distal part of the passage is most preferably within the cavity and exposed to the lumen when the female luer thread engages the male luer thread of the catheter adapter. The distal part substantially fills the cavity reducing the hydraulic column volume in the lumen and the passage. The distal part can align the passage therethrough with the lumen. The proximal part has a valve to selectively occlude the passage thereat for isolating pressure head conditions therebeyond.

A method for using a connector carrying a sensor in a passage therethrough with an adapter for a catheter may have the steps of placing a catheter into a human or animal to provide access to the dynamic pressure therein through an adapter in fluid communication therewith. Then the step of measuring atmospheric pressure with a sensor carried on a connector in a passage therethrough is performed. Setting the signal response of the sensor measurement to a datum for atmospheric pressure applied to first and second sides of the sensor is the next step. Then the step of attaching the connector to the adapter to fit the distal part into a cavity in the adapter aligns the passage with a lumen of the catheter. Gas within the cavity and the passage is allowed to escape to provide a hydraulic column substantially free of gas between the human or animal and the sensor. The step of allowing the gas to escape may include using a threaded connection between the connector and adapter to provide controlled seepage during the process of allowing the gas to escape. The additional step of occluding the passage near the proximal part may eliminate external pressure input.

BRIEF DESCRIPTION OF THE DRAWINGS

FIG. 6 is a side view in cross section of a catheter adapter and its catheter for the purpose of providing the relative cooperative relationship of the catheter adapter and the connector for the sensor mount.

DETAILED DESCRIPTION OF THE DRAWINGS

Figure 1:
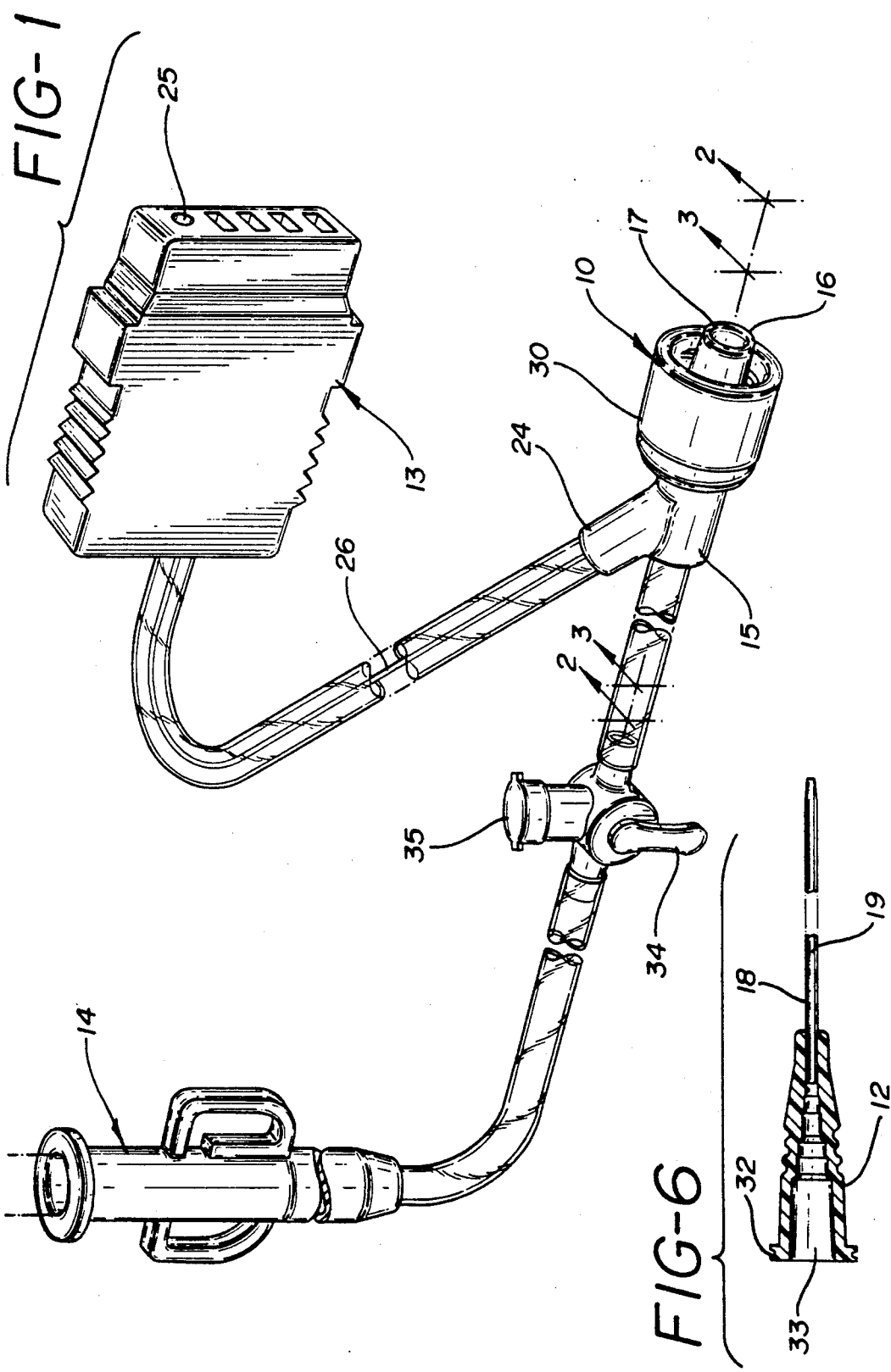
FIG. 1 is a perspective view of the preferred embodiment of a mount for a sensor including the electrical and hydraulic connections.

While this invention is satisfied by embodiments in many different forms, there is shown in the drawings and will herein be described in detail, a preferred embodiment of the invention and an alternate, with the understanding that the present disclosure is to be considered as exemplary of the principles of the invention and is not intended to limit the invention to the embodiments illustrated. The scope of the invention will be measured by the appended claims and their equivalents.

FIG. 1 is a perspective view of a connector 10. As shown in FIGS. 2, 3, 4, 5 and 6, a sensor 11 is carried in connector 10 for placement in a catheter adapter 12. Electrical and hydraulic attachment points 13 and 14, respectively are shown for clarity and understanding of the environment. The connector 10 has a proximal part 15 and a distal part 16 with a passage 17 therethrough. The distal part 16 is shaped to detachably connect with and fit within the adapter 12 for a catheter 18 when the connector 10 is attached to the adapter 12. As used throughout this specification proximal means away from the patient and toward the medic and distal means toward the patient and away from the medic. The passage 17 is thereby placed in fluid communication with and near a lumen 19 of the catheter 18, see FIG. 6. Sensor 11 mounts on the connector 10 within the distal part 16 thereof and exposed to the passage 17 for fluid communication with the lumen 19. The sensor 11 is preferably is a pressure responsive semiconductor.

Figure 2:
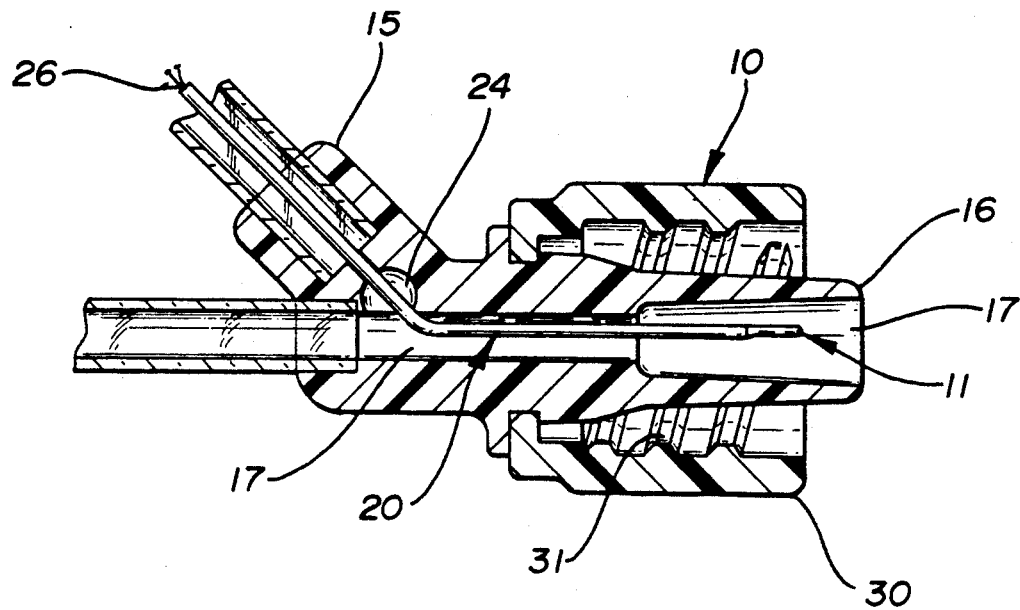
FIG. 2 is a side view of the connector of FIG. 1 partially in cross section as taken along line 2—2 of FIG. 1 and showing the mount for the sensor within the connector.
Figure 4:
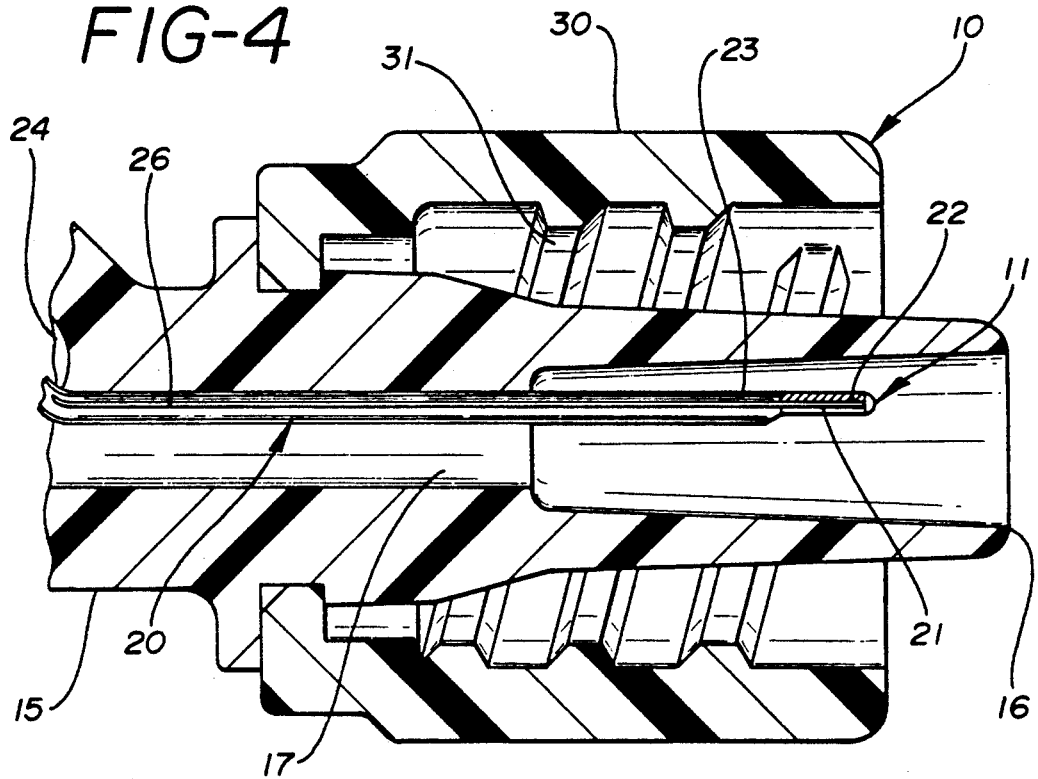
FIG. 4 is an enlarged side view in cross section of the distal part of the connector of FIG. 2 wherein the details of the mounting of the sensor ar shown.

The sensor 11, in the preferred embodiment shown in FIGS. 2 and 4, is mounted on a tube 20 extending within the passage 17 and partially through the distal part 16. The sensor 11 is positioned on the tube 20 to monitor pressure with a first side 21 of the sensor 11 exposed to the passage 17 and a second side 22 of the sensor 11 covering a channel 23 through the tube 20, as shown in FIG. 4. The tube 20 extending through the passage 17 from the sensor 11 to an exit 24 from the connector 10 near the proximal part 15. The channel 23 is vented to an atmospheric pressure source 25 on attachment point 13 beyond the exit 24. The channel 23 includes a sensor signal communication means 26 connected to the sensor 11 and passing through the tube 20 for transmitting signals from the sensor 11 through the exit 24. A catheter pressure assembly is described and claimed in a patent application, U.S. Ser. No. 246,476 and a member to support the sensor is described and claimed in a patent application, U.S. Ser. No. 410,564; the disclosures of those applications are incorporated herein by reference.

The signal communication means 26 includes a plurality of conductors insulated from one another and arranged to transmit electrical signals from the sensor 11 through the exit 24. A multiconductor and support is described and claimed in a patent application, U.S. Ser. No. 524,105; the disclosure of that application is incorporated herein by reference.

Figure 3:
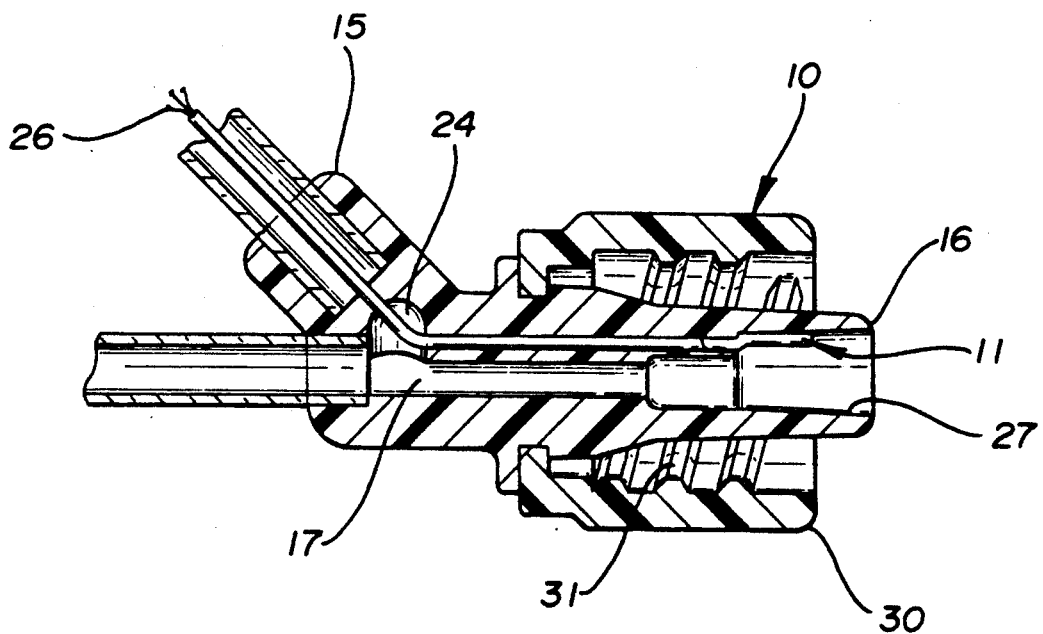
FIG. 3 is a partially side view of the connector of FIG. 1 in cross section as taken along line 3—3 of FIG. 1 and showing an alternate mount for the sensor within the connector.
Figure 5:
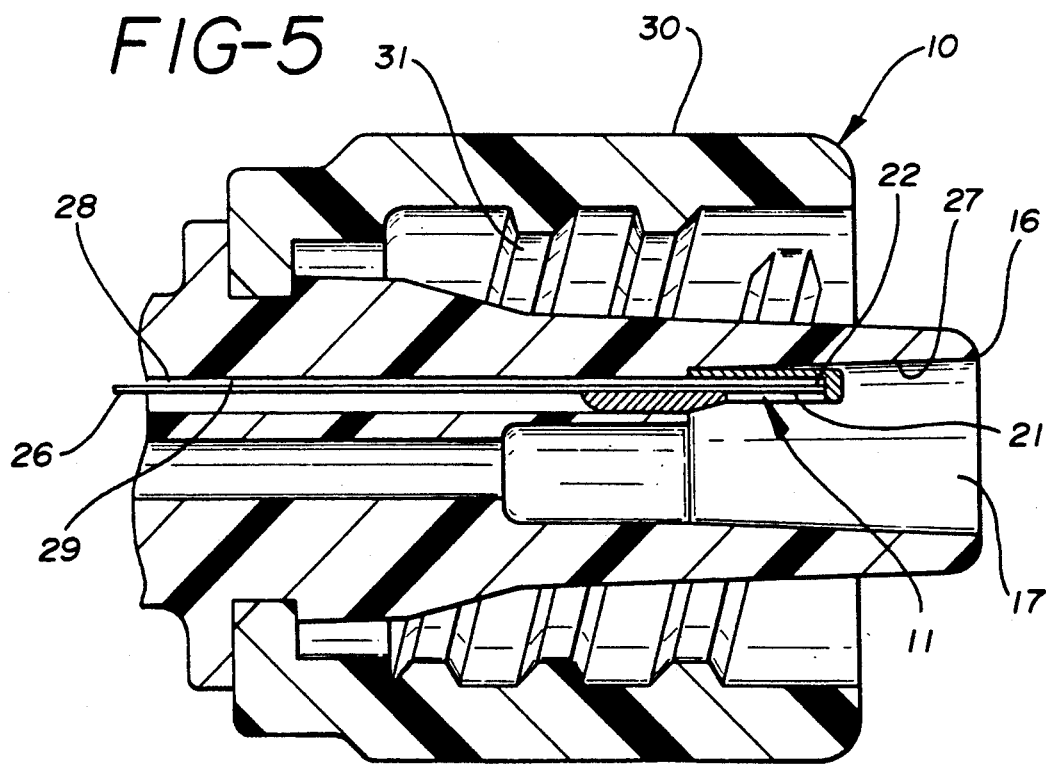
FIG. 5 is an enlarge side view in cross section of the distal part of the connector of FIG. 3 wherein the details of the mounting of the sensor are shown.

In FIGS. 3 and 5 the sensor 11 is shown mounted to an inside wall 27 of the passage 17 within the distal part 16 thereof. As the alternate embodiment is essentially identical to the preferred embodiment, except for the mounting of the sensor 11, the reference numbers used will be the same. Only different components will have different numbers. The sensor 11 may be located substantially within the inside wall 27 as long as the first side 21 thereof is exposed to the passage 17 and the second side 22 covers an opening 28 through the inside wall 27 that is vented at its exit 24 near the proximal part 15 to atmospheric pressure. The opening 28 most preferably extends within the inside wall from the sensor to the proximal part 15. The opening 28 is in the embodiment shown in FIG. 5 a groove 29 containing the sensor signal communication means 26 passing therewithin and therethrough for transmitting signals from the sensor 11 through the exit 24. As an alternate construction the signal communication means 26 of sensor 11 may be used to seals the groove 29 separating the pressure in the passage 17 from the pressure in the groove 29.

The connector 10 shown in the FIGS. 1 through 5 has a sleeve 30 with a female luer thread 31; the sleeve 30 is rotatably carried about the proximal part 15. The sleeve 30 extends distally for threaded engagement with a male luer thread 32 of the adapter 12. The sleeve 30 and adapter 12 thereby can be threaded together to lock to one another allowing fluid tight communication between a cavity 33 within the adapter 12 and the passage 17. The distal part 16 of the connector 10 is within the cavity 33 and exposing passage 17 to the lumen 19 when the female luer thread 31 engages the male luer thread 32 of the adapter 12. The distal part 16 substantially fills the cavity 33 reducing the hydraulic column volume of the lumen 19 and the passage 17. The distal part 16 aligns the passage 17 therethrough with the lumen 19. As shown in FIG. 1 the proximal part 15 has a valve 34 to selectively occlude the passage 17 thereat for isolating pressure head conditions therebeyond.

Preferably valve 34 is a threeway valve provided to connect a side port 35 on the valve to either the passage 17 or the hydraulic attachment point 14 as desired. Side port 35 can be used with a syringe (not shown) in a well known manner to easily make injections or withdraw samples because the passage 17 can be connected to the syringe by the three way valve 34. While the three way valve 34 is shown in FIG. 1 located proximal to the connector 10, it could be integral with the proximal part 15 thereof thus eliminating the tubing between the connector 10 and the valve 34. As an alternate the valve 34 could be a separate component with or without the side port 35 and having luer fittings so that placement between the adapter 12 and the connector 10 could be made if desired.

A method for using the connector 10 to carry the sensor 11 in the passage 17 therethrough with the adapter 12 for the catheter 18 has the step of placing the catheter 18 into a human or animal to provide access to the dynamic pressure therein and through the adapter 12 which is in fluid communication therewith. The method measures atmospheric pressure with the sensor 11 carried on the connector 10 in the passage 17 extending from the distal part 16 to the proximal part 15 prior to connection with, by insertion into the adapter 12. The method continues with the step of setting the signal response of the measurement of sensor 11 to a datum for atmospheric pressure applied to the first and second sides 21 and 22 of the sensor 11. The next step of the preferred method includes attaching the connector 10 to the adapter 12 to fit the distal part 16 into the cavity 33 in the adapter 12 and to align the passage 17 with the lumen 19 of the catheter 18. Finally the step allows gas within the cavity 33 and the passage 17 to escape to provide a hydraulic column substantially free of gas between the human or animal and the sensor 11.

The step of allowing the gas to escape may include using threaded connections such as 31 and 32 between the connector 10 and adapter 12 to provide controlled seepage during the step of allowing the gas to escape. The additional step of occluding the passage 17 near the proximal part 15 may be used to eliminate external pressure input from the first side 21 of the sensor 11.

The preferred and alternate constructions shown in FIGS. 2 and 4 and FIGS. 3 and 5, respectively, are designed to simplify the rezeroing of the sensor 11 by the selective attachment of the connector 10 to a placed catheter 18 if desired. The connector 10 allows free flow of medication of body samples through passage 17, subject only to the position of valve 34. Complicated apparatus for rezeroing and special handling of a catheter with a sensor at its tip are eliminated by connector 10. Signal response and ease of use are enhanced over an external pressure sensor since the hydraulic column volume is minimized and easily debubbled.

What is claimed is:

1. A connector for connecting a medical catheter to peripheral equipment, the catheter comprising an adapter and a lumen, the connector comprising:
   a proximal part for connection to the peripheral equipment, a distal part for connection to the adapter and a passage between the proximal and distal parts, the distal part being shaped to detachably connect with the adapter, the distal part comprising connection means for connecting the connector to the adapter, such that the connector, when attached to the adapter places the passage in fluid communication with the lumen of the catheter, and
   a sensor mounted in the passage and substantially within the connecting means and exposed to the passage for fluid communication with the lumen.

2. The connector of claim 1 further comprising a tube extending towards the distal part substantially within the passage and partially into the distal part, the tube being provided with a bore and, the sensor being connected to the tube, wherein the sensor comprises a first side exposed to the passage and a second side in fluid communication with the bore, and the tube extending through the passage from the sensor towards the proximal part.

3. The connector of claim 2 wherein the tube comprises a vent to atmospheric pressure.

4. The connector of claim 2 further comprising a valve means to selectively occlude the passage.

5. The connector of claim 3 further comprising a seal on the tube to separate the pressure in the passage from the pressure in the bore.

6. The connector of claim 4 further comprising sensor signal communication means for transmitting information from the sensor.

7. The connector of claim 1 wherein the sensor comprises a first side and a second side and wherein the sensor is mounted to an inside wall of the passage, the first side of the sensor being exposed to the passage and the proximal part of the connector comprising a vent for venting the second side of the sensor to atmospheric pressure.

8. The connector of claim 7 wherein the inside wall is provided with an opening, the opening extending within the inside wall of the passage from the sensor to the proximal part of the connector and the second side of the sensor covering the opening.

9. The connector of claim 8 further comprising sensor signal communication means for transmitting information from the sensor and wherein the opening is a groove for accommodating the sensor signal communication means.

10. The connector of claim 8 further comprising a seal on the tube for separating the pressure in the passage and the pressure in the opening.

11. The connector of claim 1 wherein the connection means comprises a sleeve including a first luer connector rotatably carried about the proximal part, the sleeve extending distally for engagement with a second luer connector of the adapter allowing fluid tight communication between the adapter and the passage.

12. A connector for carrying a sensor for use with a medical catheter, the catheter comprising an adapter and a lumen, the connector comprising:
   a proximal part, a distal part a passage therebetween and a vent to atmospheric pressure near the proximal part, the distal part shaped to detachably connect with and fit the adapter for a catheter, the connector when attached to the adapter placing the passage in fluid communication with the lumen of the catheter;
   a sleeve with a first luer connector carried about the proximal part and extending distally for engagement with a second luer connector on the adapter allowing fluid tight communication between the adapter and the passage, the distal part substantially filling the adapter thereby reducing hydraulic column volume in the lumen and the passage and the distal part aligning the passage with the lumen;
   a sensor mounted to an inside wall of the passage within the distal part and located substantially within the inside wall, the sensor including a pressure responsive semiconductor with a first side exposed to the passage for fluid communication with the lumen and a second side covering the vent to atmospheric pressure near the proximal part, and
   a sensor signal communication means connected to the semiconductor and passing through the vent for transmitting signals from the sensor.

* * * * *